United States Patent [19]

Farmer et al.

[11] Patent Number: 5,942,643
[45] Date of Patent: Aug. 24, 1999

[54] METHOD FOR THE MANUFACTURE OF N-PHOSPHONOMETHYLGLYCINE FROM N-PHOSPHONOMETHYLIMINODIACETIC ACID USING A LOW TEMPERATURE CATALYTIC CARBON

[75] Inventors: Richard W. Farmer, Gibsonia; Robert H. Vaughn, Bethel Park, both of Pa.

[73] Assignee: Calgon Carbon Corporation, Pittsburgh, Pa.

[21] Appl. No.: 09/078,748

[22] Filed: May 14, 1998

[51] Int. Cl.[6] .................................................. C07F 9/22
[52] U.S. Cl. ............................ 562/17; 502/439; 502/418
[58] Field of Search .............................. 562/17; 502/439, 502/418

[56] References Cited

U.S. PATENT DOCUMENTS 3,969,398  7/1976  Hershman .
4,147,719  4/1979  Franz .
4,579,689  4/1986  Hershman .
4,624,937  11/1986  Chou ........................................ 502/180
5,179,228  1/1993  Ramon ...................................... 562/17

FOREIGN PATENT DOCUMENTS 19500121  1/1995  Germany .

Primary Examiner—Gary Geist
Assistant Examiner—Jean F. Vollano
Attorney, Agent, or Firm—Titus & McConomy LLP

[57] ABSTRACT

An improved process is provided for the manufacture of N-phosphonomethylglycine from N-phophonomethyliminodiacetic acid in the presence of a molecular-oxygen containing gas utilizing a catalytically active carbonaceous char produced at low temperature. The improvement is provided by the use of a carbonaceous char capable of rapidly decomposing hydrogen peroxide in an aqueous solution.

7 Claims, 2 Drawing Sheets

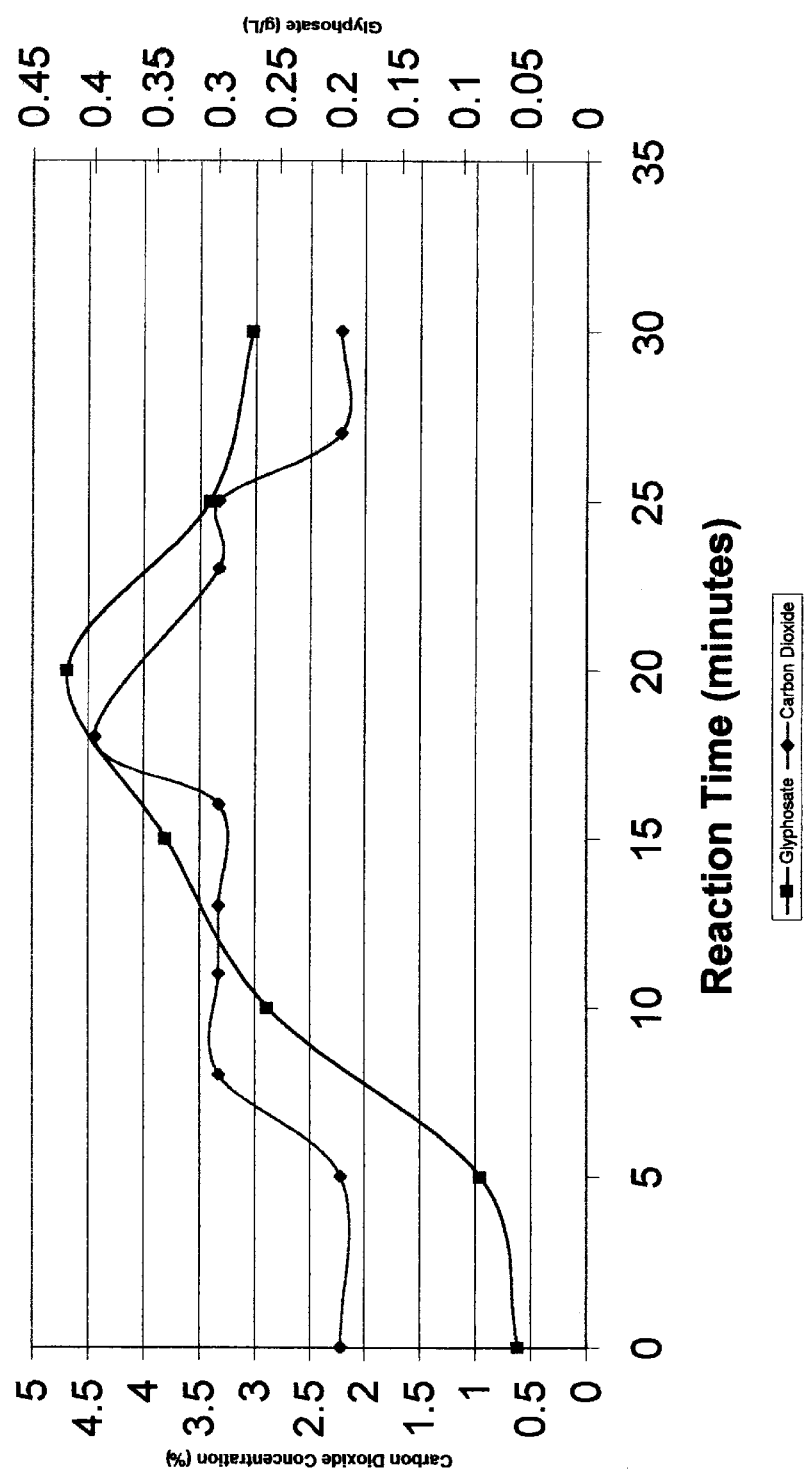

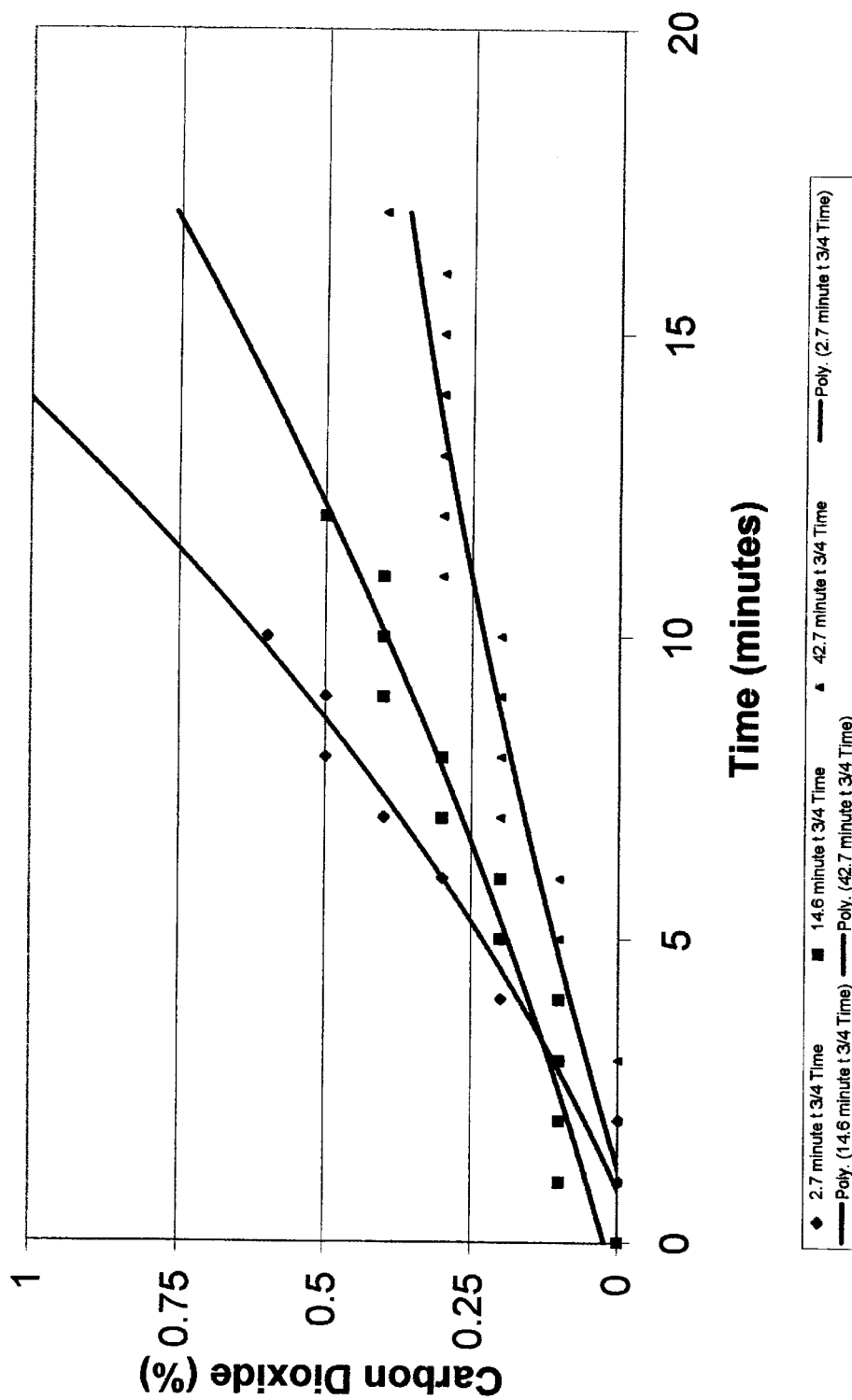

METHOD FOR THE MANUFACTURE OF N-PHOSPHONOMETHYLGLYCINE FROM N-PHOSPHONOMETHYLIMINODIACETIC ACID USING A LOW TEMPERATURE CATALYTIC CARBON

FIELD OF INVENTION

The present invention relates the use of a catalytically active carbonaceous char produced at low temperature for the manufacture of N-phosphonomethylglycine from N-phosphonomethyliminodiacetic acid in the presence of a molecular oxygen containing gas.

BACKGROUND OF THE INVENTION

The use of activated carbon as a catalyst to promote the formation of glyphosate by oxidation of N-phosphonomethyliminodiacetic acid is described by Hershman, U.S. Pat. No. 3,969,398, where N-phosphonomethyliminodiacetic acid is prepared by reacting iminodiacetic acid with formaldehyde and phosphoric acid. Hershman reports teaching that glyphosate is produced by the oxidation of N-phosphonomethyliminodiacetic acid in the presence of activated carbon as a catalyst according to the following proposed reaction:

$C_5H_{10}O_7NP + \frac{1}{2}O_2 \rightarrow C_3H_8O_5NP + CO_2 + CH_2O$

Rogers et al., U.S. Pat. No. 5,578,190 describes the use of carbon impregnated with various metals. The impregnated carbon is utilized to facilitate a hydrogenation reaction to produce glyphosate.

Cullen et al., International Publication Number WO 96/38455, describes the oxidation of N-phosphonomethyliminodiacetic acid with an oxidizing agent such as hydrogen peroxide in the presence of activated carbon as a catalyst. The oxidation reaction results in the production of glyphosate.

Chou, U.S. Pat. No. 4,624,937, describes the process for modifying an activated carbon capable of oxidizing tertiary amines and secondary amines in the presence of activated carbon. The process describes the modification of the activated carbon by an oxygen-containing gas and ammonia at temperatures from 800° to 1200° C. The modification process enhances the ability of the activated carbon to facilitate the oxidation of the tertiary or secondary amines.

All of the prior art for improving the production of glyphosate from N-phosphonomethyliminodiacetic acid has certain disadvantages, which make the process unattractive from a commercial standpoint. Chief among these is an inability to determine in a rapid and convenient manner the suitability of a char for such applications prior to its use, in particular the intrinsic catalytic activity of the char for glyphosate manufacture. As a result of this shortcoming, it is not possible to know or even to estimate during the preparation of a char the utility of the final product short of actual testing in the application itself.

Accordingly, it is the object of the present invention to provide an improved process for the manufacture of N-phosphonomethylglycine from N-phosphonomethyliminodiacetic acid in the presence of a molecular oxygen containing gas such as pure oxygen by contacting said media with a carbonaceous char produced at temperatures lower than 600° C. in which the intrinsic catalytic activity of the char is measured and known prior to use.

SUMMARY OF THE INVENTION

In general, the present invention comprises an improved process for the manufacture of N-phosphonomethylglycine from N-phosphonomethyliminodiacetic acid in the presence of a gas containing molecular oxygen, such as pure oxygen, by contacting said acid with a carbonaceous char produced at temperatures less than 600° C. in which the intrinsic catalytic activity of the char is measured and known prior to use. More specifically, the carbonaceous char is preferably the low temperature char described in Ser. No. 09/079,424, filed May 14, 1998. The improvement provided by the present invention is in the use such carbonaceous char, which can rapidly decompose hydrogen peroxide in aqueous solution. The rate of hydrogen peroxide decomposition is measured by the test described in U.S. Pat. No. 5,470,748 and is reported, except where noted, as the t-¾ time, measured in minutes.

The process of the present invention is preferably carried out at a temperature between about 25° C. and 90° C. and most preferably about 70° C. In the present invention it is found that catalytically-active chars produced at temperatures less than 600° C. produce glyphosate at a more favorable rate than standard commercially available activated carbons. Other advantages of the invention will become apparent from a perusal of the following detailed description of a presently preferred embodiment taken in connection with the accompanying drawings.

BRIEF DESCRIPTION OF THE DRAWINGS

FIG. 1 is a graphical illustration the carbon dioxide concentration in the off-gas and the glyphosate in the reactor liquid; and FIG. 2 is a graphical illustration of the improvement in the production of glyphosate using an activated low temperature catalytically active carbon char over commercially available carbons used for the same purposes.

PRESENTLY PREFERRED EMBODIMENTS

The utility of the invention is demonstrated in the following two examples. Example 1 demonstrates the correlation between the carbon dioxide concentration in the reactor off-gas and the glyphosate concentration in the reactor liquid. Example 2 demonstrates the the improved process using a low temperature catalytically-active activated carbon medium catalyst.

EXAMPLE 1

A sample of catalytically active material was sized so that 95% of the particles passed through a 325 mesh Tyler screen. A 0.2 gram sample of the pulverized carbon was added to the stainless steel reactor vessel of the Autoclave Engineers Eze-Seal™ Autoclave. A 0.5 gram aliquot of N-phosphonomethyliminodiacetic acid was added to the reaction flask along with 95 milliliters of deionized water. The stainless steel reactor was connected to the autoclave, and the slurry stirred at 200 rpm under a nitrogen blanket. The slurry was heated externally to 70° C. The slurry was allowed to equilibrate for approximately two hours prior to initiation of the oxidation reaction. After reaching equilibrium, pure oxygen was introduced to the reactor flask at a pressure of 60 psi. The off-gas from the reactor flask was monitored using a Nova Model 7550P7 Multi-Gas Analyzer. Liquid samples were periodically withdrawn from the reactor vessel through a sample port and analyzed for glyphosate concentration though the use of a Waters HPLC. The peak carbon dioxide concentration occurred after 18 minutes while the peak glyphosate concentration occurred at 20 minutes. A graphic illustration the carbon dioxide concentration in the off-gas and the glyphosate in the reactor liquid is shown in FIG. 1.

EXAMPLE 2

Samples of a low temperature catalytically-active material and the commercially available material (Filtrasorb 400, Calgon Carbon Corporation, Pittsburgh, Pa.), with similar properties other than catalytic activity as measured by the t-¾ time at pH 7, were sized so that 95% of the particles passed through a 325 mesh Tyler screen. A 0.2 gram sample of the pulverized carbon was added to the stainless steel reactor vessel of the Autoclave Engineers Eze-Seal™ Autoclave. A 0.5 gram aliquot of N-phosphonomethyliminodiacetic acid was added to the reaction flask along with 95 milliliters of deionized water. The stainless steel reactor was connected to the autoclave, and the slurry stirred at 200 rpm under a nitrogen blanket. The slurry was heated externally to 70° C. The slurry was allowed to equilibrate for approximately two hours prior to initiation of the oxidation reaction. After reaching equilibrium, pure oxygen was introduced to the reactor flask at a pressure of 60 psi. The off-gas from the reactor flask was monitored using a Nova Model 7550P7 Multi-Gas Analyzer. Data show the catalytically-active material (t-¾ time 4.8 minutes) produced at temperatures less than 600° C. generate carbon dioxide at a rate greater than the commercially available activated carbon Filtrasorb 400 (t-¾ time 49 minutes), FIG. 2.

While a presently preferred embodiment of the invention has been shown and described in particularity, it may be otherwise embodied within the scope of appended claims.

What is claimed is:

1. In a process for the production of N-phosphonomethyl glycine which comprises contacting an aqueous solution of N-phosphonomethyliminodiacetic acid with a gas containing molecular oxygen at a temperature sufficiently elevated to initiate and sustain reaction in the presence of a catalyst, the improvement therein comprising using a low temperature catalytically active carbonaceous char produced by the steps of (a) combining a nitrogen-containing material with a carbon-containing material to produce a mixture, (b) carbonizing said mixture at an elevated temperature less than 600° C., (c) oxidizing said carbonized mixture during or after said carbonization at temperatures less than 600° C., and (d) increasing the temperature of the carbonized and oxidized mixture to above 600° C. to provide a low temperature catalytically active carbonaceous char.

2. The improvement set forth in claim 1 including contacting the product of step (c) with a nitrogen-containing compound, said compound having at least one nitrogen containing functionality in which the nitrogen exhibits a formal oxidation number of less than zero, during or before step (d).

3. The improvement set forth in claim 1 or 2 including the step of (e) activating said low temperature catalytically active carbonaceous char by raising the temperature to above 600° in the presence of $H_2O$, $CO_2$, or $O_2$ or combinations thereof to provide an activated low temperature catalytically active carbonaceous char.

4. The improvement set forth in claim 1 or 2 wherein steps (b) and (c) are performed together to produce a low temperature catalytically active carbonaceous char.

5. The improvement set forth in claim 1 wherein said catalytically active carbonaceous char is granular, pelleted, shaped, or powdered.

6. The improvement set forth in claim 1 wherein said catalytically active carbonaceous is formed, bonded, or otherwise incorporated into a unitized body for use as a filtration media.

7. The improvement set forth in claim 1 wherein said catalytically active carbonaceous char is a fiber, fabric, or cloth.

* * * * *